United States Patent [19]
Ruddy et al.

[11] Patent Number: 5,360,604
[45] Date of Patent: Nov. 1, 1994

[54] X-RAY CONTRAST COMPOSITIONS CONTAINING AN ORGANIC CRYSTALLINE X-RAY CONTRAST AGENT IN COMBINATION WITH PHARMACEUTICALLY ACCEPTABLE CLAYS

[75] Inventors: Stephen B. Ruddy, Schwenksville; Mary E. Roberts, Downingtown; Gregory L. McIntire, West Chester; Eugene R. Cooper, Berwyn; Carl R. Illig, Phoenixville, all of Pa.

[73] Assignee: Sterling Winthrop Inc., Malvern, Pa.

[21] Appl. No.: 247,424

[22] Filed: May 23, 1994

Related U.S. Application Data

[63] Continuation-in-part of Ser. No. 227,423, Apr. 14, 1994.

[51] Int. Cl.$^5$ .............................................. A61K 49/04
[52] U.S. Cl. .................................. 424/5; 514/54; 514/57; 514/717; 514/941; 514/942; 128/654
[58] Field of Search ................... 424/5, 4; 514/54, 57, 514/717, 941, 942, 580, 656; 128/654; 423/328

[56] References Cited

U.S. PATENT DOCUMENTS

| | | | |
|---|---|---|---|
| 2,622,100 | 12/1952 | Newbery et al. | 260/612 |
| 2,659,690 | 11/1953 | Slaybaugh | 167/95 |
| 2,680,089 | 6/1954 | Lowy | 167/95 |
| 2,832,722 | 8/1958 | Singher | 167/95 |
| 3,192,118 | 6/1965 | Battista et al. | 167/95 |
| 4,069,306 | 1/1978 | Rothman | 424/4 |
| 4,120,946 | 10/1978 | Queuille et al. | 424/4 |
| 4,588,574 | 5/1986 | Felder et al. | 423/554 |
| 4,692,325 | 9/1987 | Kritzler | 424/4 |
| 4,927,624 | 5/1990 | Bryant et al. | 424/9 |
| 5,019,370 | 5/1991 | Jay et al. | 424/4 |
| 5,107,842 | 5/1992 | Levene et al. | 128/662.02 |
| 5,122,363 | 6/1992 | Balkus, Jr. et al. | 424/9 |
| 5,277,896 | 1/1994 | Balkus, Jr. et al. | 424/9 |
| 5,318,768 | 6/1994 | Illig et al. | 424/5 |
| 5,326,553 | 7/1994 | Illig et al. | 424/5 |

OTHER PUBLICATIONS

Wang et al, Yaoxne Xuebao, vol. 16, No. 8, pp. 610–617, Aug. 1981.
James et al, Pharm. Acta Helvetiae, 47, 224–256 (1972).

*Primary Examiner*—Gary E. Hollinden
*Attorney, Agent, or Firm*—Arthur Rosenstein; Imre Balogh

[57] ABSTRACT

Disclosed are x-ray contrast compositions for oral or retrograde examination of the gastrointestinal tract comprising a crystalline organic constrast agent in combination with a pharmaceutically acceptable clay in a pharmaceutically acceptable carrier; and methods for their use in diagnostic radiology of the gastrointestinal tract.

20 Claims, No Drawings

X-RAY CONTRAST COMPOSITIONS CONTAINING AN ORGANIC CRYSTALLINE X-RAY CONTRAST AGENT IN COMBINATION WITH PHARMACEUTICALLY ACCEPTABLE CLAYS

CROSS REFERENCE TO RELATED APPLICATION

This is a continuation-in-part of application Ser. No. 08/227,423 filed on Apr. 14, 1994.

BACKGROUND OF THE INVENTION

1. Field of the Invention

This invention relates to an x-ray contrast composition for oral or retrograde administration to a mammal comprising particles consisting essentially of a crystalline organic x-ray contrast producing agent in combination with pharmaceutically acceptable clays.

2. Reported Developments

Roentgenographic examination utilizing x-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate x-ray radiation. D. P. Swanson et al in "Pharmaceuticals In Medical Imaging", 1990, MacMillan Publishing Company, provides an excellent background in medical imaging utilizing contrast agents and compositions therewith.

Roentgenographic examination of the GI tract are indicated for conditions of digestive disorders, changes in bowel habit, abdominal pain, GI bleeding and the like. Prior to radiological examination, administration of a radiopaque contrast medium is necessary to permit adequate delineation of the respective lumen or mucosal surface from surrounding soft tissues. Accordingly, a contrast medium is administered orally to visualize the mouth, pharynx, esophagus, stomach, duodenum and proximal small intestine. The contrast medium is administered rectally for examination of the distal small intestine and the colon.

The most widely used contrast agent for the visualization of the GI tract is barium sulfate administered as a suspension orally or rectally as an enema. (See, for example, U.S. Pat. Nos. 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids it lacks homogeneity and poorly adheres to mucus membranes which can result in poor x-ray images. In the colon, when administered as an enema, it flocculates and forms irregular clumps with fecal matter.

Iodinated organic compounds have also been used as GI contrast agents since the iodine atom is an effective x-ray absorber. They have the most versatility and are utilized in the widest variety of procedures. They are very absorptive of x-rays with which the iodine interacts and produce a so-called photoelectric effect which is a large magnification in contrast caused by the photons stopped in the iodine-containing medium. The magnification of contrast exceeds the level that would be expected from relative changes in density. Because of this magnification, relatively low concentrations of the contrast agent can be utilized. (For iodinated agents see, for example, U.S. Pat. Nos. 2,786,055; 3,795,698; 2,820,814; 3,360,436; 3,574,718, 3,733,397; 4,735,795 and 5,047,228.)

The desiderata for an ideal GI contrast agent includes: good toxicological profile; the ability to fill the entire bowel/lumen and evenly coat the gut mucosa so that the presence of the bowel is detectable when the lumen is not distended; and nonirritation to the intestinal mucosa; and passage through the GI tract without producing artifacts or stimulating vigorous intestinal peristalsis.

These requirements were addressed by many investigators and their efforts resulted in great improvements over the years. The requirement of evenly coating the gut mucosa with a contrast agent to effectively cover the walls of the intestines proved to be rather difficult. Without meeting these requirements it is impossible to obtain x-ray pictures of high precision. To that end, the use of certain polymer additives were proposed as illustrated hereunder.

U.S. Pat. No. 4,069,306 discloses an x-ray contrast preparation which is said to adhere to the walls of body cavities. The preparation comprises a finely divided water-insoluble inorganic x-ray contrast agent and minute particles of a hydrophilic polymer which is insoluble in water but is water-swellable. The body cavity is supplied with such preparation suspended in water. The x-ray contrast agent is present in admixture with and/or enclosed in and/or adhered to said minute polymer particles.

U.S. Pat. No. 4,120,946 discloses a pharmaceutical composition for barium opacification of the digestive tract, comprising colloidal barium sulfate and a polyacrylamide in an aqueous vehicle. The polyacrylamide forms a viscous solution at low concentration which makes it possible to maintain the barium sulfate in suspension and at the same time permit good adherence of the preparation to the walls of the organ which it is desired to x-ray.

U.S. Pat. No. 5,019,370 discloses a biodegradable radiographic contrast medium comprising biodegradable polymeric spheres which carry a radiographically opaque element, such as iodine, bromine, samarium and erbium. The contrast medium is provided either in a dry or liquid state and may be administered intravenously, orally and intra-arterially.

While these polymeric materials greatly enhance attachment of the contrast agent used therewith to the walls of organs for better visualization thereof, they do not provide a uniform coating thereon. As such, there is still a need for an improved x-ray imaging medium that uniformly coats the soft tissues subjected to diagnostic x-ray examination.

We have now discovered that certain organic crystalline x-ray contrast agents in combination with pharmaceutically acceptable clays provide excellent x-ray imaging medium.

SUMMARY OF THE INVENTION

It is the object of the present invention to provide compositions for coating the gastrointestinal tract of mammals to form an effective radiopaque coating thereon by which diagnostic examination of the GI tract may be accomplished.

The object of the present invention is achieved by a composition comprising: an organic x-ray contrast agent in particulate form in combination with a pharmaceutically acceptable clay in a pharmaceutically acceptable vehicle.

In accordance with the invention there is further provided a method for x-ray diagnostic imaging of the GI tract which comprises orally or rectally administering to the patient an effective amount contrast producing amount of the above-described x-ray contrast compositions.

A method for diagnostic imagining of the GI tract for use in medical procedures in accordance with this invention comprises orally or rectally administering to the mammalian patient in need of x-ray examination, an effective contrast producing amount of a composition of the present invention. After administration, at least a portion of the GI tract containing the administered composition is exposed to x-rays to produce an x-ray image pattern corresponding to the presence of the contrast agent, then the x-ray image is visualized and interpreted using techniques known in the art.

DETAILED DESCRIPTION OF THE INVENTION

Starting materials, reagents and solvents can be obtained from chemical suppliers, such as Aldrich, Baker, DuPont and Eastman Chemical Companies, or they may be prepared by techniques known in the prior art.

The x-ray contrast agent useful in the practice of this invention is non-radioactive and exists as a discrete, crystalline phase of an organic substance. The crystalline phase differs from an amorphous or non-crystalline phase which results from solvent precipitation techniques such as described in U.S. Pat. No. 4,826,689 noted above. The organic substance can be present in one or more suitable crystalline phases. The invention can be practiced with a wide variety of crystalline, non-radioactive x-ray contrast agents. However, the x-ray contrast agent must be poorly soluble and dispersible in at least one liquid medium. By "poorly soluble", it is meant that the agent has a solubility in the liquid dispersion medium, e.g., water, of less than about 10 mg/ml, and preferably of less than about 1 mg/ml. The preferred liquid dispersion medium is water. Additionally, the invention can be practiced with other liquid media in which the selected x-ray contrast agent is poorly soluble and dispersible, including, for example, aqueous saline solutions, such as phosphate buffered saline (PBS), plasma, mixed aqueous and nonaqueous solutions, for example, water and alcohol, and suitable nonaqueous solvents such as alcohol, glycerol and the like.

The x-ray contrast agent can be an iodinated compound. The iodinated compound can be aromatic or nonaromatic. Aromatic compounds are preferred. The iodinated compound can comprise, one, two, three or more iodine atoms per molecule. Preferred species contain at least two, and more preferably, at least three iodine atoms per molecule. The iodinated compounds selected can contain substituents that do not impart solubility to the compound, such as, for example, alkylureido, alkoxyacylamido, hydroxyacetamido, butyrolactamido, succinimido, trifluoroacetamido, carboxy, carboxamido, hydroxy, alkoxy, acylamino, and the like substituents.

A preferred class of contrast agents includes various esters and amides of iodinated aromatic acids. The esters preferably are alkyl or substituted alkyl esters. The amides can be primary or secondary amides, preferably alkyl or substituted alkyl amides. For example, the contrast agent can be an ester or amide of a substituted triiodobenzoic acid such as an acyl, carbamyl, and/or acylmethyl substituted triiodobenzoic acid. Illustrative representative examples of iodinated aromatic acids include, but are not limited to, diatrizoic acid, metrizoic acid, iothalamic acid, trimesic acid, urokonic acid, ioxaglic acid (hexabrix), ioxitalamic acid, tetraiodoterephthalic acid, iodipamide, icarmic acid, and the like.

Many of the iodinated molecules described above, if in monomeric form, can also be prepared as dimers (sometimes referred to as bis compounds), trimers (sometimes referred to as tris compounds), etc., by techniques known in the art. It is contemplated that this invention can be practiced with poorly soluble-iodinated compounds in monomeric, dimeric, trimeric and polymeric forms. Representative illustrative compounds are described by Sovak, cited above, pages 40–53.

Classes of preferred contrast agents have the following structural formulae:

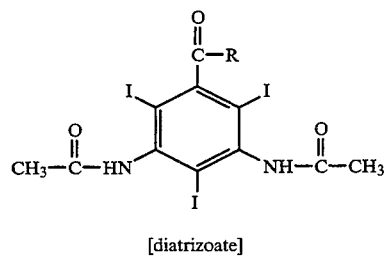

[diatrizoate]

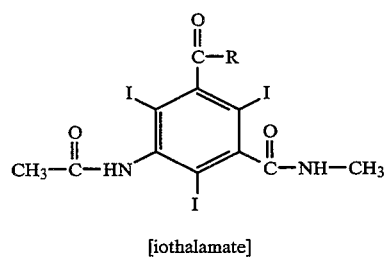

[iothalamate]

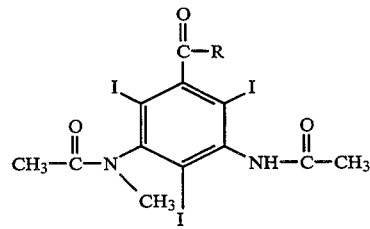

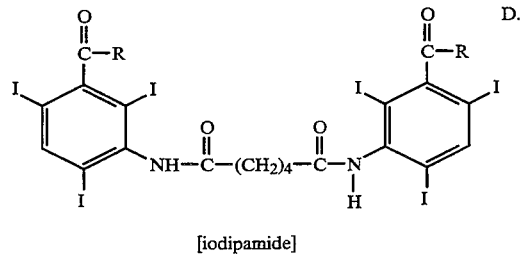

[iodipamide]

In the above structures, R can be OR¹,

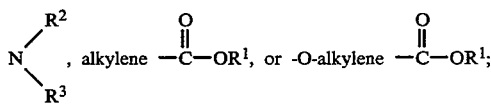

wherein $R^1$ is alkyl, and $R^2$ and $R^3$ are independently H or alkyl.

Each alkyl group can independently contain from 1–20, preferably 1–8, and more preferably, 1–4 carbon atoms.

The alkylene group preferably contains from 1 to 4 carbon atoms such as methylene, ethylene, propylene and the like.

Particularly preferred contrast agents include the ethyl ester of diatrizoic acid, i.e., ethyl 3,5-diacetamido-2,4,6-triiodobenzoate, also known as ethyl 3,5-bis-(acetylamino)-2,4,6-triodobenzoate or ethyl diatrizoate, having the structural formula A above wherein R=—OCH$_2$CH$_3$(WIN 8883); the ethyl glycolate ester of diatrizoic acid, i.e., ethyl (3,5-bis(acetylamino)-2,4,6-triiodobenzoyloxy)acetate, also known as ethyl diatrizoxyacetate, having the structural formula A above wherein

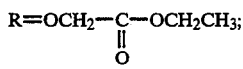

and ethyl 2-(3,5-bis(acetylamino)-2,4,6-triiodobenzoyloxy)butyrate, also known as ethyl 2-diatrizoxybutyrate.

In addition, the invention can be practiced in conjunction with the water insoluble iodinated carbonate esters described in PCT/EP90/00053.

The above described x-ray contrast agents are known compounds and/or can be prepared by techniques known in the art. For example, water-insoluble esters and terminal amides of acids such as the abovedescribed iodinated aromatic acids can be prepared by conventional alkylation or amidation techniques known in the art. The above-noted acids and other acids which can be used as starting materials are commercially available and/or can be prepared by techniques known in the art. The examples which follow contain illustrative examples of known synthetic techniques.

EXAMPLE 1

Synthesis of Ethyl 3,5-bis(acetylamino)-2,4,6-triiodobenzoate

To 8.11 L of dry N,N-dimethylformamide was added 1.01 kg (1.65 mol) of diatrizoic acid. To the vigorously stirred suspension was carefully added 274 g (1.99 tool) of milled potassium carbonate. During the addition there was significant gas evolution. Before all of the suspended solid had gone into solution, a second solid began to form toward the end of the carbonate addition. The mixture was stirred for 30 min. at room temperature. Ethyl iodide (608 g, 3.90 mol) was added dropwise and the mixture was stirred overnight at room temperature at which point the reaction mixture was nearly homogeneous. The reaction was poured into 25 L of water, filtered and the solid washed with water and dried at reduced pressure at 60° C. to afford 962 g (91% yield) of a white solid, mp 280°–290° C. (dec.). Analysis for $C_{13}H_{13}I_3N_2O_4$: Calculated/Found: C, 24.32/24.27; H, 2.05/1.93; N, 4.36/4.28.

EXAMPLE 2

Synthesis of Ethyl (3,5-bis(acetylamino)-2,4,6-triiodo-benzoyloxy)acetate

To 175 mL of dry N,N-dimethylformamide (DMF) was added 63.6 g (0.100 mol) sodium diatrizoate and 14.7 g (0.120 mol) of ethyl chloroacetate and the mixture was heated on a steam bath for 6 hr. The reaction was filtered while hot and the filtrate cooled to room temperature and diluted to 500 ml with water. The mixture was cooled and filtered and the collected solid washed with water. The solid was then dissolved in 350 ml hot DMF, filtered and added to an equal volume of water. The mixture was cooled, filtered, washed with water, and the solid dried at 100° C. overnight to afford 53.0 g (76% yield) of a white powder, mp 269.5°–270.5° C. Analysis for $C_{15}H_{15}I_3N_2O_6$: Calculated/Found: C, 25.73/25.80; H, 2.15/2.77; I, 54.4/53.8.

EXAMPLE 3

Synthesis of Ethyl 2-(3,5-bis(acetylamino)-2,4,6-triiodobenzoyloxy)butyrate

To 500 mL of dry N,N-dimethylformamide was added 159 g (0.250 mol) sodium diatrizoate and 54.5 g (0.280 mol) of ethyl 2-bromobutyrate. The mixture was heated on a steam bath for 20 h, cooled to room temperature and poured into 3 L of dilute ammonium hydroxide. The solid was filtered, washing with water, and air-dried. The solid was further purified by crystallization from 50% aqueous ethanol (after treatment with decolorizing carbon) affording two crops which were dried at 100° C. overnight to afford 121 g (66%) of a white powder, m.p. 288°–290° C. (dec.). Analysis for $C_{17}H_{19}I_3N_2O_6$: Calculated/Found: C, 28.05/28.36/H, 2.63/2.55; I, 52.3/52.3.

The particles useful in the practice of this invention include a surface modifier. Surface modifiers useful herein physically adhere to the surface of the x-ray contrast agent but do not chemically react with the agent or itself. Individually adsorbed molecules of the surface modifier are essentially free of intermolecular crosslinkages. Suitable surface modifiers can be selected from known organic and inorganic pharmaceutical excipients such as various polymers, low-molecular weight oligomers, natural products and surfactants. Preferred surface modifiers include nonionic and anionic surfactants. Representative examples of surface modifiers include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, and polyvinylpyrrolidone (PVP). Most of these surface modifiers are known pharmaceutical excipients and are described in detail in the *Handbook of Pharmaceutical Excipients,* published jointly by the American Pharmaceutical Association and The Pharmaceutical Society of Great Britain, the Pharmaceutical Press, 1986, the disclosure of which is hereby incorporated by reference in its entirety.

Particularly preferred surface modifiers include polyvinylpyrrolidone, tyloxapol, poloxamers such as Pluronic F68 and F108, which are block copolymers of ethylene oxide and propylene oxide, and poloxamines such as Tetronic 908 (also known as Poloxamine 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OT, which is a dioctyl ester of sodium sulfosuccinic acid, available from American Cyanamid, Duponol P, which is a sodium lauryl sulfate, available from DuPont, Triton X-200, which is an alkyl aryl polyether sulfonate, available from Rohm and Haas, Tween 80, which is a polyoxyethylene sorbitan fatty acid ester, available from ICI Specialty Chemicals, and Carbowax 3350 and 934, which are polyethylene glycols available from Union Carbide. Surface modifiers which have been found to be particularly useful include Tetronic 908, the Tweens, Pluronic F-68 and polyvinylpyrrolidone.

Other useful surface modifiers include:

decanoyl-N-methylglucamide;
n-decyl β-D-glucopyranoside;
n-decyl β-D-maltopyranoside;
n-dodecyl β-D-glucopyranoside;
n-dodecyl β-D-maltoside;
heptanoyl-N-methylglucamide
n-heptyl β-D-glucopyranoside;
n-heptyl β-D-thioglucoside;
n-hexyl β-D-glucopyranoside;
nonanoyl-N-methylglucamide;
n-nonyl β-D-glucopyranoside;
octanoyl-N-methylglucamide;
n-octyl β-D-glucopyranoside;
octyl β-D-thioglucopyranoside;

and the like. A particularly preferred class of surface modifiers includes water-soluble or water-dispersible compounds having the formula $$L\begin{matrix} \text{CONCH}_2(\text{CHOH})_x\text{CH}_2\text{OH} \\ | \\ R^1 \\ \\ \text{CONCH}_2(\text{CHOH})_y\text{CH}_2\text{OH} \\ | \\ R^2 \end{matrix}$$

wherein

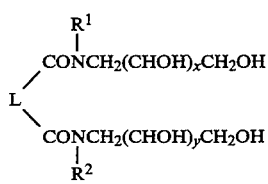

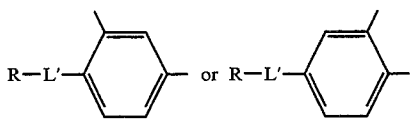

L' is a chemical bond, —O—, —S—, —NH—, —CONH— or —SO$_2$NH—;

R is a hydrophobic substituted or unsubstituted alkyl, substituted or unsubstituted cycloalkyl, or a substituted or unsubstituted aryl group;

each of R$^1$ and R$^2$ independently is hydrogen or an alkyl group having from 1 to 4 carbon atoms;

each of a and b independently is 0 or an integer from 1 to 3, provided that the sum of a and b is not greater than 3; and, each of x and y independently is an integer from 3 to 7.

Preferred compounds within this class conform to the above structure wherein R contains from 6 to 36 carbon atoms, for example, R is an n-alkyl group containing from 6 to 18 carbon atoms, each of R$^1$ and R$^2$ independently is a methyl, ethyl, propyl or butyl group and a is 0 and b is 0. This class of surface modifiers is described in U.K. Patent Application No. 9104957.7 filed Mar. 8, 1991 and can be prepared by reacting an appropriate dicarboxylic acid ester with an appropriate monosaccharide amine, preferably in the absence of a solvent, at a reaction temperature from 140° to 200° C.

The surface modifiers are commercially available and/or can be prepared by techniques known in the art. Two or more surface modifiers can be used in combination.

The particles useful in the practice of this invention can be prepared in accordance with the wet grinding process described in U.S. Pat. No. 5,145,684 which is incorporated herein by reference. The process comprises dispersing a poorly soluble x-ray contrast agent in a liquid dispersion medium and wet-grinding the agent in the presence of grinding media to reduce the particle size of the contrast agent to an effective average particle size of from about 0.05μ to about 100μ, preferably of from about 0.05μ to about 5μ and most preferably from about 0.1μ to about 1μ. The particles can be reduced in size in the presence of a surface modifier. Alternatively, the particles can be contacted with a surface modifier after attrition.

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of from about 0.05μ to about 100μ" is meant that at least 90% of the particles have a weight average particle size of from about 0.05μ to about 100μ when measured by the above-noted techniques. The particle size range allows sufficient number of particles' distribution in the film forming composition when the GI tract is coated therewith, yet insures against absorption through the intestinal walls.

The natural, pharmaceutically acceptable clays incorporated in the present invention comprise aluminum silicates. They are used in purified form, suitable for administration to patients. The natural, pharmaceutically acceptable clays of the present invention, generally referred to as smectities, consist of dioctohedral smectites and trioctahedral smectites.

Dioctahedral smectites include:
montmorillonite, having the formula $$M^+Al_{3y}(FeMg)_y Si_4O_{10}(OH)_2 \cdot nH_2O;$$

beidelite, having the formula $$M^+(Al_2(Si_{4-x}Al_x)O_{10}(OH)_2 \cdot nH_2O;$$

nontronite, having the formula $$M^+(Fe_2^{3+}(Si_{4-x}Al_x)O_{10}(OH)_2 \cdot nH_2O;$$

wherein $M^+$ is Na, Ca or Mg.

Trioctahedral smectites include:
saponite, having the formula $$M^+(Mg_{3-y}(AlFe)_y)Si_{4-x}Al_x)O_{10}(OH)_2 \cdot nH_2O; \text{ and}$$

hectorite, having the formula $$M^+(Mg_{3-y}Li_y)Si_4O_{10}(OH)_2 \cdot nH_2O;$$

wherein $M^+$ is Na, Ca or Mg.

The clays are available from chemical suppliers, such as, for example, American Colloid Company, Arlington Heights, Ill., under the tradenames:
MAGNABRITE®HS;
HECTABRITE®DP,
HECTABRITE®LT,
CARMARGO®White,
POLARGEL®NF,
POLARGEL®HV, and
VOLCLAY®NF-BC.

Other suppliers include: Engelhard Corp., Iselin, N.J.; Ashland Chemical Inc., Colombus, Ohio; RT Vanderbilt Co., Inc., Norwalk, Conn. and Whittaker Clark & Daniels, Inc., S. Plainfield, N.J.

The contrast agent and the pharmaceutically acceptable clay are formulated for administration using physiologically acceptable carriers or excipients in a manner within the skill of the art. The contrast agent with the addition of pharmaceutically acceptable aids (such as surfactants and emulsifiers) and excipients may be suspended or emulsified in an aqueous medium resulting in a suspension or emulsion.

Compositions of the Present Invention

Compositions of the present invention comprise the following pharmaceutically acceptable components based on % w/v:

| Ingredients | Broad Range | Preferred Range | Most Preferred Range |
|---|---|---|---|
| Contrast agent | 5–45 | 10–35 | 15–25 |
| Clay | 0.1–10 | 0.5–5 | 1–2 |
| Surfactant | 1–20 | 2–10 | 3–5 |
| Excipients | 0–15 | 0.5–5 | 1–2 |

Water - q.s. to 100% by volume

Excipients contemplated by the present invention include antifoaming agents, such as simethicone, siloxyalkylene polymers and polyoxyalkylated natural oils; preservatives, such as methyl paraben, propyl paraben, benzoic acid and sorbic acid; flavoring/sweetening agents, such as sodium saccharine; and coloring agents, such as lakes and dyes.

While the organic crystalline contrast agents of the present invention in formulations with a pharmaceutically acceptable vehicle provide good quality x-ray images, the addition of a pharmaceutically acceptable clay to the formulations greatly increases the quality of the x-ray images. At the low extreme of the concentration range there is little or no benefit gained, while above the higher extreme of the concentration range the formulation is too viscous for administration.

The following formulation examples will further illustrate the invention.

EXAMPLE 4

| Components | |
|---|---|
| Ethyl 3,5-bis(acetylamino)-2,4,6-triiodobenzoate | 22.00 g |
| HECTABRITE ®DP | 1.50 g |
| Sorbitan Monostearate | 0.70 g |
| Polysorbate 60 (Tween 60) | 1.20 g |
| Poloxamer 338 | 4.00 g |
| Sodium Saccharine | 0.30 g |
| Benzoic Acid | 0.50 g |
| Sorbic Acid | 0.05 g |
| Water q.s. to make 100 ml | |

EXAMPLE 5

| Components | |
|---|---|
| Ethyl (3,5-bis(acetylamino)-2,4,6-triiodobenzoyloxy) acetate | 22.50 g |
| POLARGEL ®NF | 2.30 g |
| Sorbitan Mono-oleate | 0.45 g |
| Polysorbate 20 (Tween 820) | 1.30 g |
| Polyvinyl Alcohol | 4.50 g |
| Sodium Saccharine | 0.25 g |
| Simethicone emulsion (food-grade) | 0.10 g |
| Water q.s. to make 100 ml | |

EXAMPLE 6

| Components | |
|---|---|
| Ethyl 2-(3,5-bis(acetylamino)-2,4,6-triiodobenzoyloxy) butyrate | 18.50 g |
| MAGNABRITE ® HS | 1.25 g |
| Sorbitan monopalmitate | 0.60 g |
| Polyoxyethylene myristyl ether | 0.60 g |
| Polyvinylpyrrolidone | 3.50 g |
| Vanilla flavoring (artificial) | 0.25 g |
| Strawberry flavoring (artificial) | 0.25 g |
| Sorbitol | 1.00 g |
| Water q.s. to make 100 ml | |

The surface active agents used in the present invention may be cationic, anionic, nonionic or zwitterionic.

Suitable cationic surfactants include cetyl trimethyl ammonium bromide, cetyl pyridinium chloride, myristyl gamma picolinium chloride and benzalkonium chloride. Suitable anionic agents include sodium lauryl sulphate, sodium heptadecyl sulphate, alkyl benzenesulphonic acids and salts thereof, sodium butylnapthalene sulfonate, and sulphosuccinates. Zwitterionic surface active agents are substances that when dissolved in water they behave as diprotic adds and, as they ionize, they behave both as a weak base and a weak acid. Since the two charges on the molecule balance each other out they act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less irritating than the cationic or anionic surfactants. Nonionic surfactants include carboxylic esters, carboxylic amides, ethoxylated alkylphenols, ethoxylated aliphatic alcohols, ethylene oxide polymer or ethylene oxide/propylene oxide co-polymers polyvinylpyrrolidone and polyvinylalcohol.

One particular type of carboxylic ester nonionic surface active agents are the partial, for example mono-, esters formed by the reaction of fatty and resin adds, for example of about 8 to about 18 carbon atoms, with polyalcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters are the condensation products of fatty and resin partial acids, for example mono-, esters ethylene oxide, such as fatty or resin acid esters of polyoxyethylene sorbitan and sorbitol, for example polyoxyethylene sorbitan, mono-tall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the ammonia, monoethylamine and diethylamine amides of fatty acids having an acyl chain of from about 8 to about 18 carbon atoms.

The ethoxylated alkylphenol nonionic surface active agents include various polyethylene oxide condensates of alkylphenols, especially the condensation products of mono-alkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include:

(a) Sorbitan esters (sold under the trade name Span) having the formula:

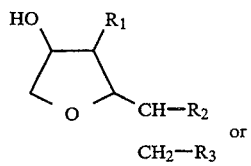

wherein
$R_1=R_2=OH$, $R_3=R$ for sorbitan monoesters,
$R_1=OH$, $R_2=R_3=R$ for sorbitan diesters,
$R_1=R_2=R_3=R$ for sorbitan triesters,
where $R=(C_{11}H_{23})COO$ for laurate,
($C_{17}H_{33}$)COO for oleate,
($C_{15}H_{31}$)COO for palmitate,
($C_{17}H_{35}$)COO for stearate;

b) Polyoxyethylene alkyl ethers (i.e. Brijs) having the formula:

$$CH_3(CH_2)_x(O-CH_2-CH_2)_yOH$$

where $(x+1)$ is the number of carbon atoms in the alkyl chain, typically:

| | |
|---|---|
| 12 lauryl | (dodecyl) |
| 14 myristyl | (tetradecyl) |
| 16 cetyl | (hexadecyl) |
| 18 stearyl | (octadecyl) | and y is the number of ethylene oxide groups in the hydrophilic chain, typically 10–60.

(c) Polyoxyethylene sorbitan fatty acid esters (Polysorbates 20, 40, 60, 65, 80 and 85) sold under the trade names of Tweens, Crillers, Sorlares and Monitans, having the formulas (1) and (2)

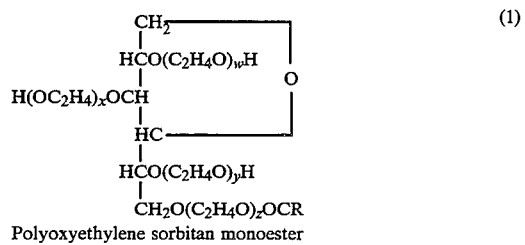
Polyoxyethylene sorbitan monoester

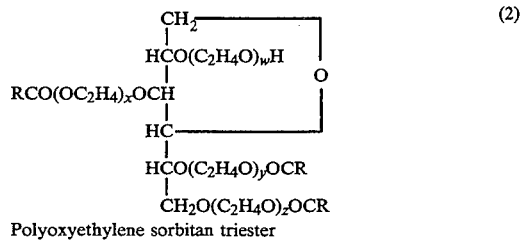
Polyoxyethylene sorbitan triester wherein $w+x+y+z=20$ (Polysorbate 20, 40, 60, 65, 80 and 85)

$w+x+y+Z=5$ (Polysorbate 81)

$w+x+y+z=4$ (Polysorbate 21 and 61).

(d) Polyoxyethylene stearates, such as:
poly(oxy-1,2-ethanediyl),α-hydro-ω-hydroxyoctadecanoate;

polyethylene glycol monostearate; and
poly(oxy-1,2-ethanediyl)-α-(1-oxooctadecyl)-ω-hydroxypolyethylene glycol monostearate.

(e) Polyethylene oxide/polypropylene oxide block co-polymers, sold under the name PLURONIC ™, which include Poloxamer 407 (PLURONIC ™ F127), Poloxamer 188 (PLURONIC ™ F68), Poloxamer 237 (PLURONIC ™ F87) and Poloxamer 338 (PLURONIC ™ F108).

(f) Polyvinylpyrrolidone.

(g) Polyvinylalcohol.

The dosages of the contrast agent used according to the method of the present invention will vary according to the precise nature of the contrast agent used. Preferably, however, the dosage should be kept as low as is consistent with achieving contrast enhanced imaging. By employing as small amount of contrast agent as possible, toxicity potential is minimized. For most contrast agents of the present invention dosages will be in the range of from about 0.1 to about 16.0 g iodine/kg body weight, preferably in the range of from about 0.5 to about 6.0 g iodine/kg of body weight, and most preferably, in the range of from about 1.2 to about 2.0 g iodine/kg body weight for regular x-ray visualization of the GI tract. For CT scanning the contrast agents of the present invention will be in the range of from about 1 to about 600 mg iodine/kg body weight, preferably in the range of from about 20 to about 200 mg iodine/kg body weight, and most preferably in the range of from about 40 to about 80 mg iodine/kg body weight.

When administered to mammals, the compositions of the present invention produce excellent x-ray and CT images.

The invention having been fully described, it will be apparent to one skilled in the art that changes and modifications can be made thereto without departing from the spirit and scope thereof.

What is claimed is:

1. An x-ray contrast composition for oral or retrograde examination comprising on a % weight per volume basis:
    (a) from about 5 to 45% of a crystalline contrast producing agent selected from the group consisting of diatrizoic acid, metrizoic acid, iothalamic acid, trimesic acid, urokonic acid, ioxathalamic acid, tetraiodoterephthalic acid, ioxaglic acid, iodipamide, ethyl-3,5-diacetamido-2,4,6-triiodobenzoate, ethyl-2-(3,5-bis(acetyl amino)-2,4,6-triiodo-benzoyloxy)butyrate, and ethyl(3,5-bis(acetylamino)-2,4,6-triiodobenzoyloxy)acetate, said crystalline contrast agent having a surface modifier adsorbed on the surface thereof in an amount sufficient to maintain an effective average particle size of from about 0.5μ to about 100μ; and
    said surface modifier is selected from the group consisting of a tetrafunctional block copolymer derived from sequential addition of propylene oxide and ethylene oxide to ethylenediamine;
    (b) from about 0.1 to 10% of a pharmaceutically acceptable clay selected from the group consisting of montmorillonite, beidelite, nontronite, hectorite and saponite;
    (c) from about 1.0 to 20% of a surfactant selected from the group consisting of nonionic, anionic, cationic and zwitterionic surfactants;
    (d) from about 0 to 15% of an excipient; and
    (e) water to make 100% by volume.

2. The x-ray contrast composition of claim 1 wherein said x-ray contrast producing agent is present in an amount of from about 10 to 35%.

3. The x-ray contrast composition of claim 1 wherein said x-ray contrast producing agent is present in an amount of from about 10 to 35%.

4. The x-ray contrast composition of claim 1 wherein said pharmaceutically acceptable clay constitutes from 0.5 to 5% of the composition.

5. The x-ray contrast composition of claim 1 wherein said surfactant constitutes from 2 to 10% of the composition.

6. The x-ray contrast composition of claim 1 wherein said excipient constitutes from 0.5 to 5% of the composition.

7. The x-ray contrast composition of claim 1 wherein said nonionic surface active agent is selected from the group consisting of carboxylic esters, carboxylic amides, ethoxylated alklyphenols, ethoxylated aliphatic alcohols, ethylene oxide polymer, ethylene oxide/propylene oxide co-polymer, polyvinylpyrrolidone and polyvinylalcohol.

8. The x-ray contrast composition of claim 1 wherein said surfactant is sorbitan ester having the formula:

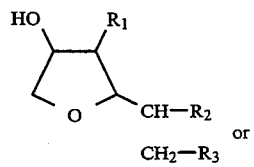

wherein
$R_1=R_2=OH$, $R_3=R$ for sorbitan monoesters,
$R_1=OH$, $R_2=R_3=R$ for sorbitan diesters,
$R_1=R_2=R_3=R$ for sorbitan triesters,
where $R=(C_{11}H_{23})COO$ for laurate,
$(C_{17}H_{33})COO$ for oleate,
$(C_{15}H_{33})COO$ for palmitate or
$(C_{17}H_{35})COO$ for stearate.

9. The x-ray contrast composition of claim 1 wherein said surface active agent is polyoxyethylene stearate.

10. The x-ray contrast composition of claim 1 wherein said surfactant is polyoxyethylene sorbitan fatty acid ester of the formulas (1) and (2)

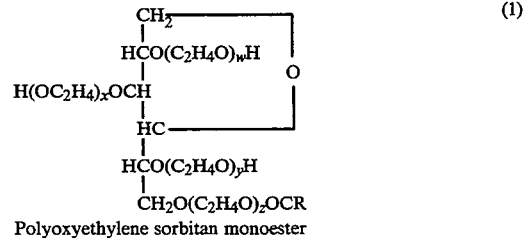

Polyoxyethylene sorbitan monoester

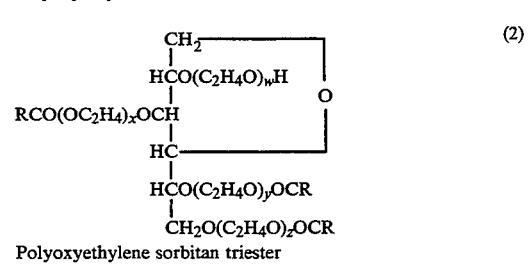

Polyoxyethylene sorbitan triester wherein $w+x+y+z=20$ $w+x+y+z=5$ $w+x+y+z=4$.

11. A method of carrying out x-ray examination of the gastrointestinal tract of a patient, said method comprises the oral or rectal
   (a) from about 5 to 45% of a crystalline contrast producing agent selected from the group consisting of diatrizoic acid, metrizoic acid, iothalamic acid, trimesic acid, urokonic acid, ioxathalamic acid, tetraiodoterephthalic acid, ioxaglic acid, iodipamide, ethyl-3,5-diacetamido-2,4,6-triiodobenzoate, ethyl-2-(3,5-bis(acetylamino)-2,4,6-triiodo-benzoyloxy)butyrate, and ethyl(3,5-bis(acetylamino)-2,4,6-triiodobenzoyloxy)acetate, said crystalline contrast agent having a surface modifier adsorbed on the surface thereof in an amount sufficient to maintain an effective average particle size of from about $0.5\mu$ to about $100\mu$; and
      said surface modifier is selected from the group consisting of a tetrafunctional block copolymer derived from sequential addition of propylene oxide and ethylene oxide to ethylenediamine;
   (b) from about 0.1 to 10% of a pharmaceutically acceptable clay selected from the group consisting of: montmorillonite, beidelite, nontronite, hectorite and saponite;
   (c) from about 1.0 to 20% of a surfactant selected from the group consisting of nonionic, anionic, cationic and zwitterionic surfactants;
   (d) from about 0 to 15% of an excipient; and
   (e) water to make 100% by volume.

12. The method of claim 11 wherein said x-ray contrast producing agent is present in an amount of from about 10 to 35%.

13. The method of claim 11 wherein said pharmaceutically acceptable clay constitutes from 0.5 to 5% of the composition.

14. The method of claim 11 wherein said surfactant constitutes from 2 to 10% of the composition.

15. The method of claim 11 wherein said surfactant constitutes from 2 to 10% of the composition.

16. The method of claim 11 wherein said excipient constitutes from 0.5 to 5% of the composition.

17. The method of claim 11 wherein said nonionic surface active agent is selected from the group consisting of carboxylic esters, carboxylic amides, ethoxylated alklyphenols, ethoxylated aliphatic alcohols, ethylene oxide polymer, ethylene oxide/propylene oxide copolymer, polyvinylpyrrolidone and polyvinylalcohol.

18. The method of claim 11 wherein said surfactant is sorbitan ester having the formula:

wherein
$R_1=R_2=OH$, $R_3=R$ for sorbitan monoesters,
$R_1=OH$, $R_2=R_3=R$ for sorbitan diesters,
$R_1=R_2=R_3=R$ for sorbitan triesters,
where $R=(C_{11}H_{23})COO$ for laurate,
$(C_{17}H_{33})COO$ for oleate,
$(C_{15}H_{31})COO$ for palmitate or
$(C_{17}H_{35})COO$ for stearate.

19. The method of claim 11 wherein said surface active agent is polyoxyethylene stearate.

20. The method of claim 11 wherein said surfactant is polyoxyethylene sorbitan fatty acid ester of the formulas (1) and (2)

Polyoxyethylene sorbitan monoester

Polyoxyethylene sorbitan triester wherein $w+x+y+z=20$ $w+x+y+z=5$ $w+x+y+z=4$

* * * * *